US00PP21770P2

(12) United States Plant Patent

Jandrew

(10) Patent No.: US PP21,770 P2
(45) Date of Patent: Mar. 8, 2011

(54) *SCAEVOLA* PLANT NAMED 'BOMY DABULE'
(50) Latin Name: *Scaevola aemula*
Varietal Denomination: Bomy Dabule

(75) Inventor: Jason Jandrew, Los Altos, CA (US)
(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/590,537

(22) Filed: Nov. 10, 2009

(51) Int. Cl.
*A01H 5/00* (2006.01)

(52) U.S. Cl. ..... Plt./363
(58) Field of Classification Search ..... Plt./363

See application file for complete search history.

*Primary Examiner*—Kent L Bell
(74) *Attorney, Agent, or Firm*—S. Matthew Edwards

(57) ABSTRACT

A new *Scaevola* plant named 'Bomy Dabule,' particularly distinguished by the violet colored flowers, good floriferousness, medium green foliage, well branched and a vigorous semi-trailing plant habit.

1 Drawing Sheet

Latin name of the genus and species of the plant claimed: *Scaevola aemula.*

Varietal denomination: 'Bomy Dabule'.

BACKGROUND OF THE NEW PLANT

The present invention comprises a new *Scaevola*, botanically known as *Scaevola aemula*, and hereinafter referred to by the variety name 'Bomy Dabule.'

'Bomy Dabule' is a product of a planned breeding program. The new cultivar has violet colored flowers, good floriferousness, medium green foliage, well branched and a vigorous semi-trailing plant habit.

'Bomy Dabule' originated from a hybridization made in August 2006 in a controlled breeding environment in Gilroy, Calif. The resultant seed was sown in January 2007. The female parent was the commercial line 'Saphira,' unpatented, with blue flowers. 'Saphira' has broader foliage and a larger flower size than 'Bomy Dabule.'

The male parent of 'Bomy Dabule' designated '204-4' was an unpatented proprietary line with blue flowers. '204-4' has a more prominent white eye and broader foliage than 'Bomy Dabule.'

'Bomy Dabule' was selected as one flowering plant within the progeny of the stated cross in the May 2007 in a controlled environment in Gilroy, Calif.

The first act of asexual reproduction of 'Bomy Dabule' was accomplished when vegetative cuttings were propagated from the initial selection in May 2007, in a controlled environment in Gilroy, Calif.

BRIEF SUMMARY OF INVENTION

Horticultural examination of plants grown from cuttings of the plant initiated in May 2007, and continuing thereafter, has demonstrated that the combination of characteristics as herein disclosed for 'Bomy Dabule' are firmly fixed and are retained through successive generations of asexual reproduction.

'Bomy Dabule' has not been observed under all possible environmental conditions. The phenotype may vary significantly with variations in environment such as temperature, light intensity and day length.

A Plant Breeder's Right for this cultivar was applied for in Canada on Jan. 30, 2009. 'Bomy Dabule' has not been made publicly available more than one year prior to the filing of this application.

The following traits have been repeatedly observed and are determined to be basic characteristics of the new variety. The combination of these characteristics distinguishes this *Scaevola* as a new and distinct variety.

BRIEF DESCRIPTION OF THE PHOTOGRAPHS

The accompanying photographic drawing shows typical flower and foliage characteristics of 'Bomy Dabule' with colors being as true as possible with an illustration of this type. The photographic drawing shows 3 flowering potted plants of the new variety growing in a 12 inch basket, and a close-up of the flower.

DETAILED BOTANICAL DESCRIPTION

The plant descriptions and measurements were taken in Gilroy, Calif. in September, 2009, from plants growing outside in a 10 inch basket, 3 plants per basket. These plants were approximately 16 weeks of age. The aforementioned photographs were taken in Gilroy, Calif. in early July 2009 from plants growing outdoors. These plants were about 12 weeks old.

Color references are made to The Royal Horticultural Society Colour Chart (R.H.S.) 2001.

TABLE 1

DIFFERENCES BETWEEN THE NEW VARIETY 'BOMY DABULE' AND A SIMILAR VARIETY

| | 'Bomy Dabule' | 'Saphira' (Unpatented) |
|---|---|---|
| Flower color: | Darker | Lighter |
| Flower size: | Smaller | Larger |
| Leaf diameter: | Narrower | Broader |

Plant:

*Form, growth and habit.*—Well branched, vigorous semi-trailing plant habit.

*Plant height.*—16-20 cm.

*Plant height (inflorescence included).*—20-25 cm.

*Plant width.*—42-50 cm.

*Garden performance and tolerance to weather.*—Very good.

*Crop time to flowering.*—About 12 weeks.

Roots:

*Number of days to initiate and develop roots.*—21-25 days at about 22 degrees C.

*Type.*—Fine, fibrous, free branching.

*Color.*—RHS N155B but whiter.

Foliage:

*Arrangement.*—Alternate, simple.

*Immature, leaf color, upper surface.*—RHS 137A.

*Lower surface.*—RHS 146B, with a little more yellow.

*Mature, leaf color, upper surface.*—RHS 146A but a little more green.

*Lower surface.*—RHS 146B with a little more yellow.

*Length.*—5.5-6.5 cm.

*Width.*—2.3-2.6 cm.

*Shape.*—Oblanceolate.

*Base shape.*—Attenuate.

*Apex shape.*—Acute.

*Margin.*—Irregularly dentate.

*Texture, upper surface.*—Glabrous, with some pilose.

*Lower surface.*—Glabrous, with some pilose.

*Color of veins, upper surface.*—About RHS 144A, but almost indistinct.

*Color of veins, lower surface.*—About RHS 144A.

*Petiole color.*—About RHS 144A with an overlay of anthocyanins of about RHS 178A.

*Length.*—1.5-2.5 cm.

*Diameter.*—0.3-0.35 cm.

*Texture.*—Glabrous, with some pilose.

Stem:

*Quantity of main branches per plant.*—About 10-14.

*Color of stem.*—RHS 146B with shades of anthocyanins of about RHS 178A on the upper facing surfaces.

*Length of stem.*—About 30 cm.

*Diameter.*—0.3 cm.

*Length of internodes.*—2.5-6.0 cm.

*Texture.*—Glabrous, with some pilose.

*Color of peduncle.*—RHS 146B with shades of anthocyanins of about RHS 178A on the upper facing surfaces.

*Length of peduncle.*—12-22 cm.

*Peduncle diameter.*—0.3-0.4 cm.

*Texture.*—Glabrous, with some pilose.

Inflorescence:

*Type.*—Solitary flowers arise from the leaf axils with one flower per leaf axil in an alternate arrangement but appearing so close together they appear to be cluster like. Each flower having 5 petals. Flowers are sessile.

*Blooming habit.*—Continuously from the Spring through late Summer.

*Quantity of flowers per inflorescence.*—About 15 open at any one time.

*Lastingness of individual blooms on the plant.*—About 6-8 days.

*Fragrance.*—None.

Bud (just before opening/showing color):

*Color.*—RHS N87C with some overlay blotching of RHS 87A.

*Length.*—1.7-1.9 cm.

*Width.*—0.3 cm.

*Shape.*—Linear.

Immature inflorescence:

*Diameter.*—2.0-2.3 cm.

*Flower color, upper surface.*—Between RHS N87B and RHS 87C ground color with RHS N87A as stripes down the middle.

*Flower color, lower surface.*—RHS N88C ground color with RHS 197A down the middle of the petal and at apex.

Mature inflorescence:

*Diameter.*—2.5-2.9 cm.

*Flower color, upper surface.*—RHS 87C ground color with RHS N87A to RHS N87B as stripes down the middle.

*Flower color, lower surface.*—RHS N88C ground color with RHS 197A down the middle of the petal and at apex.

*Petal length.*—1.2-1.4 cm.

*Petal width.*—0.3-0.4 cm.

*Petal shape.*—Elliptical.

*Apex shape.*—Apiculate.

*Margin.*—Entire.

*Petal texture, upper surface.*—Papillose.

*Petal texture, lower surface.*—Glabrous.

*Corolla tube shape.*—Open.

*Corolla length.*—1.0-1.2 cm.

*Corolla width.*—0.3-0.4 cm.

*Throat color, inside.*—RHS N144A with RHS 176B veins and RHS 183A at the side margins.

*Throat color, outside.*—RHS 44C with RHS 199D stripes.

*Corolla texture, inside.*—Pilose and a few glandular hairs.

*Corolla texture, outside.*—Pilose.

Sepals:

*Type.*—Composed of one larger and somewhat fleshy sepal and two narrow sepals, fused at the base.

*Color of sepals.*—RHS 145A, both surfaces.

*Length of long sepal.*—1.2 cm.

*Width of long sepal.*—0.3 cm.

*Length of narrow sepals.*—0.7 cm.

*Width of narrow sepals.*—0.1 cm.

*Sepal shape.*—Acicular.

*Apex shape.*—Acute.

*Margins.*—Entire.

*Texture, upper surface.*—Pilose.

*Texture, lower surface.*—Pilose.

Reproductive organs:

*Pistil.*—1.

*Length.*—1.2 cm.

*Style color.*—RHS N155 B but whiter base with RHS 187A at the upper end.

*Style length.*—0.9-1.0 cm.

*Stigma color.*—RHS N144D.

*Stigma texture.*—Villous.

*Stamens.*—5 protruding from the flower throat.

*Color of filaments.*—RHS 155B.

*Length filaments.*—0.5 cm.

*Anther color.*—RHS 155B.

*Anther length.*—0.1 cm.

*Anther shape.*—Narrowly ovate.

*Color of pollen.*—RHS 155B.

*Pollen amount.*—Sparse.

*Fertility/seed set.*—Has not been observed on this hybrid.

Disease/pest resistance: Resistance or susceptibility has not been observed on this hybrid.

What is claimed is:

1. A new and distinct variety of *Scaevola* plant named 'Bomy Dabule,' substantially as illustrated and described herein.

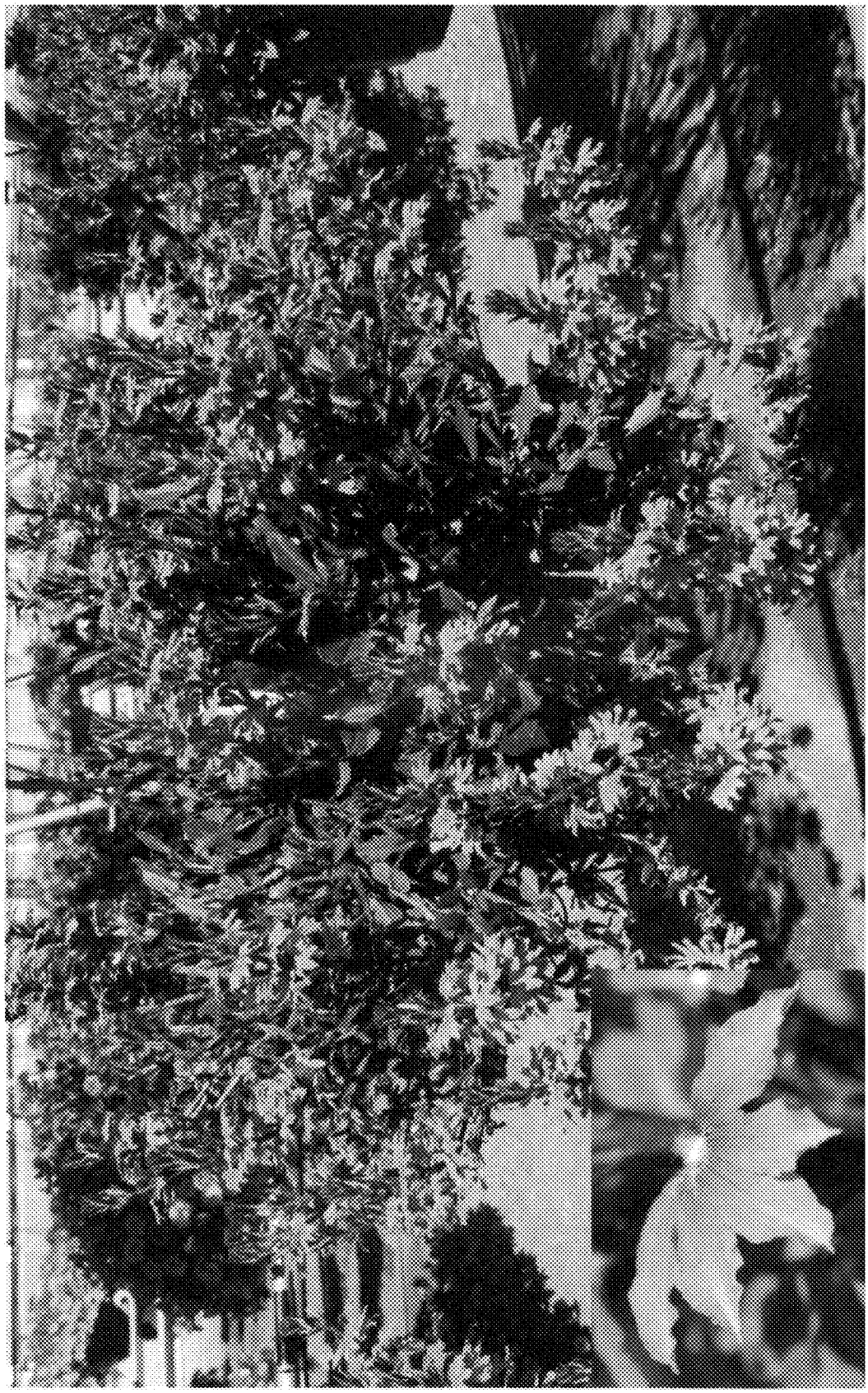

* * * * *